(12) United States Patent
Kano et al.

(10) Patent No.: US 8,093,301 B2
(45) Date of Patent: Jan. 10, 2012

(54) ANTI-ALLERGIC AGENT

(75) Inventors: Hiroshi Kano, Odawara (JP); Syuji Ikegami, Odawara (JP)

(73) Assignee: Meiji Co., Ltd., Tokyo (JP)

( * ) Notice: Subject to any disclaimer, the term of this patent is extended or adjusted under 35 U.S.C. 154(b) by 231 days.

(21) Appl. No.: 12/064,917

(22) PCT Filed: Aug. 25, 2006

(86) PCT No.: PCT/JP2006/316704
§ 371 (c)(1),
(2), (4) Date: Feb. 26, 2008

(87) PCT Pub. No.: WO2007/023935
PCT Pub. Date: Mar. 1, 2007

(65) Prior Publication Data
US 2009/0281187 A1 Nov. 12, 2009

(30) Foreign Application Priority Data
Aug. 26, 2005 (JP) .................. 2005 245672

(51) Int. Cl.
*A61K 31/192* (2006.01)
*A61K 31/136* (2006.01)
*A61K 31/122* (2006.01)
*A61P 37/08* (2006.01)

(52) U.S. Cl. .................. 514/682; 514/569; 514/657

(58) Field of Classification Search .................. None
See application file for complete search history.

(56) References Cited

U.S. PATENT DOCUMENTS

| 5,565,491 A | * | 10/1996 | Schieven | 514/492 |
| 6,524,627 B1 | * | 2/2003 | Kim et al. | 424/741 |
| 2005/0137261 A1 | | 6/2005 | Okada et al. | |

FOREIGN PATENT DOCUMENTS

| CN | 1382043 A | | 11/2002 |
| CN | 1539019 A | | 10/2004 |
| EP | 0 033 215 A2 | | 8/1981 |
| JP | 8-92082 | | 4/1996 |
| JP | 1003628 | * | 7/1996 |
| JP | 2000-116356 | | 4/2000 |
| JP | 2003-252786 | | 9/2003 |
| WO | WO 98/48839 | * | 11/1998 |

OTHER PUBLICATIONS

STN Seach Notes for U.S. Appl. No. 12/064,918, containing the English Abstract for Sato et al, pp. 5 and 6 excepted (Researched Sep. 2009 with abstract found for Jul. 1996).*
Kinhult et al., Clin Exp Allergy, 33:1141-1146, 2003.*
Kimura I. et al: "Menaquinone (Vitamin K2) Therapy for Bronchial Asthma," I. Mechanism of Action of Menaquinone on Allergic Reactions, Acta Medica Okayama, vol. 29, No. 1, pp. 73-81, 1975.
Goreg P. et al: "Antiinflammatory and Antianaphylactic Action of Vitamins K1 and K3", Arzeimittel-Forschung, vol. 18, No. 2, pp. 227-230, 1968.
Sok D.et al: "Studies on Slow Reacting Sunstances," Chem. Nat. Prod., Proc. Sino-Am. Symp., pp. 94-103, 1980.
Lien et al: "Synthesis and Antiplatelet, Antiinflammatory, and Antiallergic Activities of 2-Substituted 3-Chloro-1,4-Naphthoquinone Derivatives", Bioorg Med Chem, vol. 5, No. 12, pp. 2111-2120, 1997.
Gallin et al: "Effects of Vitamin K on Human Neutrophil Function", Journal of Immunology, vol. 128, No. 3, pp. 1399-408, 1982.
Lien et al: "Synthesis and Antiplatelet, Antiinflammatory and Antiallergic Activities of 2,3-Disubstituted 1,4-Naphthoquinones", Chem. Pharm. Bull, vol. 44, No. 6, pp. 1181-1187, 1996.
Gotthard et al: "Studies on 1,4-Naphthoquinones." 5. Mechanism of the Antianaphylactic Activity of Plumbagin, Pharmazeutische Zeitung, vol. 127, No. 40, pp. 2108-2110,1982.
Ishiguro et al: "An Approach to New Anti-Allergy Medicines Originating From Impatients Balsamina" Foods and Food Ingredients Journal of Japan, vol. 209, No. 1, pp. 13-25, 2004.
Kawamura et al: Effects of 2-Methyl-1,4-Naphtoquinone (Menadione) on Cellular Signaling in RBL-2H3 Cells, Biol Pharm Bull, Apl. vol. 29, No. 4, pp. 605-607, 2006.
Hiroshi et al: "Propionic Acid Kin Hakko Taisha Sanbutsu No Datsukaryu Yokusei Sayo" Annual Meeting of JSBBA Koen Yoshishu, p. 43, 2006.
Yoshikawa et al., Research Report (2002-2003), "High-Tech Research Center" Project, Ministry of Education, Culture, Sports, Science and Technology—Japan; -Pharmacognosy-, Anti-allergic components in Natural drug of Thailand "Khaa," [online], Apr. 2004, Kyoto Pharmaceutical University, [retrieved: Aug. 2, 2005], Internet URL:http://www.kyoto-phu.ac.ip/hitech/a5.pdf.
Hisae Oku, et al., "Antipruritic Effects of 1,4-Naphthoquinones and Related Compounds", Biological & Pharmaceutical Bulletin, vol. 25, No. 1, Jan. 2002, pp. 137-139.
Office Action issued Aug. 2, 2010, in Chinese Patent Application No. 200680030817.7.

* cited by examiner

Primary Examiner — James D Anderson
Assistant Examiner — Bong-Sook Baek
(74) Attorney, Agent, or Firm — Oblon, Spivak, McClelland, Maier & Neustadt, L.L.P.

(57) ABSTRACT

The inventors have found that vitamin K3 and vitamin K5 which may be used in pharmaceuticals and foods or ACNQ, DHNA, or the like which can stimulate the growth of bifidobacteria can inhibit degranulation of basophil-like cells, exhibit a potent degranulation-inhibiting effect, and are useful anti-allergic agents or foods. The present invention provides an anti-allergic agent containing, as an active ingredient, one or more species selected from among 2-amino-3-carboxy-1,4-naphthoquinone, 1,4-dihydroxy-2-naphthoic acid, 1,4-naphthoquinone, 4-amino-2-methyl-1-naphthol, 2-methyl-1,4-naphthoquinone, 2-amino-3-chloro-1,4-naphthoquinone, and a salt thereof.

5 Claims, 2 Drawing Sheets

ANTI-ALLERGIC AGENT

TECHNICAL FIELD

The present invention relates to an anti-allergic agent which exhibits a β-hexosaminidase release inhibitory activity and which mitigates allergic symptoms.

BACKGROUND ART

In recent years, an increased number of people have experienced onset of an allergic symptom(s) caused by specific pollen(s), food(s), etc., and this has become an object of public concern. As a result, development of an anti-allergic agent or food for mitigating an onset allergic symptom continues to be an object of great interest.

Meanwhile, therapeutic methods for allergic symptoms are generally divided into steroid therapies based on, for example, administration of a steroid hormone, and non-steroid therapies employing an anti-histaminic agent or the like. Of these, steroid therapies are highly effective for mitigating allergic symptoms. However, administration of a steroid for a long period of time may cause adverse side effects such as osteoporosis, cataract, and thrombosis.

The onset mechanism of allergic symptoms has already been elucidated. Specifically, granulocytes such as basophils and mast cells contain chemical mediators such as histamine. When a specific site of the surfaces of such granulocytes is stimulated by an antigen, degranulation occurs, whereby the chemical mediators are released to the outside of the cells. The thus-released chemical mediators induce allergic symptoms such as sneezing, snivel, lacrymation, dermatitis, and asthma.

Since the onset mechanism of allergic symptoms has been elucidated, attempts, in addition to reduction in IgE level, have been made to discover a drug for non-steroid therapy from, for example, extracts of natural products. Such drugs inhibit degranulation of mast cells and basophils, which would otherwise occur through binding of IgE to a high-affinity IgE receptor (FcεRI) expressed on the surfaces of mast cells and basophils and subsequent cross-linking by an antigen.

Examples of such drugs include α- or γ-mangostin, which is present in a mangosteen peel extract (see Patent Document 1); epigallocatechin-3-O-gallates present in tea extracts (see Non-Patent Document 1); a benzophenone derivative "sulochrin" which is produced by Fungus *Oospora* as a kind of fungus (see Patent Document 2); a diterpene "forskolin" which is extracted from a *Perilla* plant (see Patent Document 3); and a phenylpropanoid extracted from dry roots of *A. galanga* (Thailand) (see Non-Patent Document 2).

Patent Document 1: JP-A-2000-116356
Patent Document 2: JP-A-8-92082
Patent Document 3: JP-A-2003-252786
Non-Patent Document 1: Maeda et al, The Journal of Immunology (2004), Vol. 172, pp. 4486-4492
Non-Patent Document 2: Yoshikawa et al., Research Report (2002-2003), "High-Tech Research Center" Project, Ministry of Education, Culture, Sports, Science and Technology—Japan; -Pharmacognosy-, Anti-allergic components in Natural drug of Thailand "Khaa," [online], April 2004, Kyoto Pharmaceutical University, [retrieved: Aug. 2, 2005], Internet <URL: http://www.kyoto-phu.ac.jp/hitech/a5.pdf>

DISCLOSURE OF THE INVENTION

Problems to be Solved by the Invention

Conventional anti-allergic agents have drawbacks such as unsatisfactory anti-allergic efficacy and adverse side effects. Thus, an object of the present invention is to provide a novel anti-allergic agent.

Means for Solving the Problems

Inhibition of degranulation of mast cells or basophils, which would otherwise occur even after binding of an IgE antibody to FcεRI, directly leads to mitigation of allergic symptoms. The degree of inhibition of degranulation of such cells may be determined by β-hexosaminidase as an index (L B Schwartz, K F Austen, and S I Wasserman, Immunologic release of beta-hexosaminidase and beta-glucuronidase from purified rat serosal mast cells, J. Immunol., (1979) 123: p. 1445-1450 and Non-Patent Document 2). Therefore, the present inventors have studied inhibition of degranulation of basophils by use of naphthoquinone compounds as test substances, and have evaluated the inhibition effect based on β-hexosaminidase release inhibitory activity and 50% β-hexosaminidase release inhibitory concentration ($IC_{50}$). As a result, the inventors have found that specific naphthoquinone compounds exhibits a potent degranulation-inhibiting effect and serves as a useful anti-allergic agent.

Accordingly, the present invention provides an anti-allergic agent containing, as an active ingredient, one, two or more species selected from 2-amino-3-carboxy-1,4-naphthoquinone, 1,4-dihydroxy-2-naphthoic acid, 1,4-naphthoquinone, 4-amino-2-methyl-1-naphthol, 2-methyl-1,4-naphthoquinone, 2-amino-3-chloro-1,4-naphthoquinone, and a salt thereof.

Effects of the Invention

The naphthoquinone compounds of the present invention, which exhibit a potent degranulation-inhibiting effect, are useful anti-allergic agents.

BEST MODES FOR CARRYING OUT THE INVENTION

Figure 1:
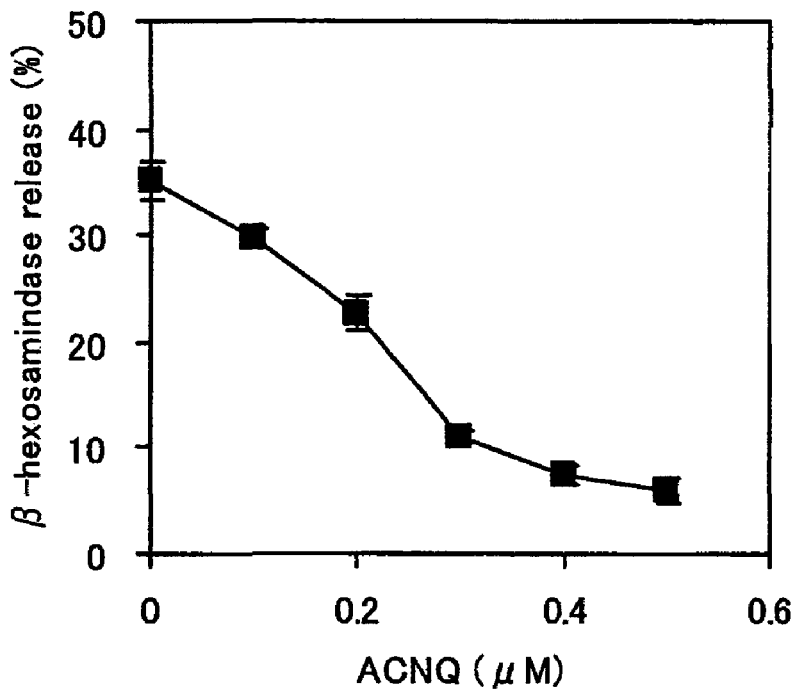
FIG. 1 Percent β-hexosaminidase release values when ACNQ was administered.

The present invention will next be described in detail.

The active ingredient of the anti-allergic agent according to the present invention is one, two or more species selected from 2-amino-3-carboxy-1,4-naphthoquinone (ACNQ), 1,4-dihydroxy-2-naphthoic acid (DHNA), 1,4-naphthoquinone, 2-methyl-1,4-naphthoquinone (vitamin K3), 4-amino-2-methyl-1-naphthol (vitamin K5), 2-amino-3-chloro-1,4-naphthoquinone, and a salt thereof. The active ingredient is preferably 2-amino-3-carboxy-1,4-naphthoquinone (ACNQ) or 1,4-dihydroxy-2-naphthoic acid(DHNA).

The above ingredient in the salt form is preferably a pharmaceutically acceptable salt or a salt acceptable in food. Examples of the salt include salts of an alkali metal such as sodium, potassium, or lithium; salts of an alkaline earth metal such as calcium, magnesium, or manganese; and acid-added salts such as hydrochlorides and sulfates.

All these ingredients are known compounds. For example, vitamin K3 and vitamin K5 are used in pharmaceuticals or foods. ACNQ and DHNA, which are known to be compounds which can stimulate the growth of bifidobacteria, are highly safe materials (JP-A-7-289273, JP-A-10-36328, JP-A-2003-89683, and JP-A-2004-210676).

The aforementioned naphthoquinone compounds, which exhibit a potent degranulation-preventing effect and has high safety, are useful as anti-allergic agents. Examples of allergic symptoms targeted by the present invention include allergic rhinitis, allergic dermatitis, asthma, sneezing, sniffling, lacrymation, and itching.

The anti-allergic agent according to the present invention may be used as is or mixed with another pharmaceutical or any pharmaceutically acceptable carrier or diluent, to thereby produce a pharmaceutical product of a desired form. Alternatively, the anti-allergic agent according to the present invention may be incorporated into a food, and the product may be used as an anti-allergic food, particularly a food labeled as "mitigating an allergic symptom."

No particular limitation is imposed on the ingredient content of the pharmaceutical product or food. However, generally, the content is preferably 0.01 to 100 wt. %, more preferably 0.1 to 50 wt. %.

The anti-allergic agent of the present invention may be produced through any production method generally employed in production of the pharmaceutical product or food. Specifically, the agent of the invention may be produced through directly mixing the ingredients for dispersion and forming into a product of a desired shape. In the production thereof, an additive (e.g., a carrier or a diluent) which is acceptable to use in the pharmaceutical product or food may be used. Specific examples thereof include solvents, solubilizers, tonicity agents, preservatives, anti-oxidants, vehicles, binders, lubricants, emulsifiers, and stabilizers.

The anti-allergic agent may be administered perorally or parenterally, for example, intramuscularly, subcutaneously, intravenously, intraperitoneally, or cutaneously. Examples of the dosage form of the agent include oral drugs, eye drops, injections, ointments, creams, and suppositories. Examples of oral drugs include tablets, granules, fine granules, hard capsules, soft capsules, powders, troches, and peroral liquids.

Examples of the anti-allergic foods include candies, drops, chewing gum, capsules, tablets, refrigerants, sweets, cold sweets, milk products, breads, rice foods, cereals, and meat products.

No particular limitation is imposed on the dose or intake amount of the anti-allergic agent according to the present invention, but the daily dose of the agent (as reduced to the aforementioned ingredient) is preferably 0.005 to 500 mg per adult.

EXAMPLES

<Induction of Degranulation in Cells>

In the Examples, the degree of cell degranulation was assessed through determination of β-hexosaminidase activity. In a specific procedure, basophil-like cells (RBL-2H3, Human Science Laboratory Resource Bank) were suspended in a Dulbecco's modified Eagle's medium (DMEM, product of Gibco) containing a 10% fetal calf serum, and the suspension was incubated overnight at 37° C. in a 96-well plate ($2.5 \times 10^5$ cells/mL) in the presence of 0.1 μg/mL anti-dinitrophenyl (DNP)-IgE antibody (product of SIGMA).

The thus-treated basophil-like cells (RBL-2H3) were washed with phosphate buffer (PBS) and further incubated at 37° C. for 30 minutes in the presence of each test substance (Examples 1 to 6 and Comparative Examples 1 to 3) at a predetermined concentration. The concentrations at which incubation was performed were 0.1, 0.2, 0.3, 0.4, and 0.5 μM (ACNQ); 20, 30, 40, 60, and 80 μM (DHNA); 60, 70, 80, 90, and 100 μM (2-methyl-1,4-naphthoquinone (vitamin K3)); 10, 20, 30, 40, and 50 μM (4-amino-2-methyl-1-naphthol (vitamin K5)); 10, 20, 30, 40, and 50 μM (1,4-naphthoquinone); 3, 4, 5, 6, and 7 μM (2-amino-3-chloro-1,4-naphthoquinone); 50 and 100 μM (vitamin K1); 25, 50, and 100 μM (vitamin K2); and 50 and 100 μM (1,3-naphthalenediol).

The thus-incubated basophil-like cells (RBL-2H3) were washed with PBS, and further incubated at 37° C. for one hour in the presence of 1-μg/mL DNP-BSA (product of SSL). After completion of incubation, a supernatant was recovered from each well, and the activity of β-hexosaminidase contained in each supernatant was determined. The activity of β-hexosaminidase remaining in the cells was also determined through solubilizing the remaining cells with 0.1% polyoxyethylene(10)octylphenyl ether/DMEM.

<Determination of β-Hexosaminidase Activity>

Each of the thus-obtained supernatants and cell solubilized liquids was added to a 96-well plate (50 μL/well), and 2 mM p-nitrophenyl N-acetyl-β-D-glucosaminide (product of SIGMA) serving as a substrate was added thereto (50 μL/well). After incubation at 37° C. for two hours, a suppressor (1M Tris, pH: 9.0) was added thereto (150 μL/well), and the absorbance at 415 nm was measured by means of a plate reader. For assessing degranulation, percent β-hexosaminidase release (%) was calculated through the following formula:

Percent β-hexosaminidase release (%)=100×($OD_{415}$ of supernatant)/($OD_{415}$ of supernatant+$OD_{415}$ of solubilized cells).

<β-Hexosaminidase Release Inhibition Test>

The β-hexosaminidase activity of supernatant was determined as described above. The β-hexosaminidase activity of a supernatant of basophil-like cells (RBL-2H3) incubated in the presence of each of the test substances of Examples 1 to 6 and Comparative Examples 1 to 3) was measured, whereby 50% β-hexosaminidase release inhibitory concentration ($IC_{50}$) was calculated.

Examples 1 and 2

In Examples 1 and 2, 2-amino-3-carboxy-1,4-naphthoquinone (ACNQ) and 1,4-dihydroxy-2-naphthoic acid (DHNA, product of Wako Pure Chemical Industries, Ltd.) were employed as test substances. Through the aforementioned procedure, β-hexosaminidase activity was determined, and β-hexosaminidase release inhibition tests were performed.

Examples 3 to 6 and Comparative Examples 1 to 3

In Examples 3 to 6, vitamin K3 (2-methyl-1,4-naphthoquinone, product of Wako Pure Chemical Industries, Ltd.), vitamin K5 (4-amino-2-methyl-1-naphthol, product of Wako Pure Chemical Industries, Ltd.), 1,4-naphthoquinone (product of Wako Pure Chemical Industries, Ltd.), and 2-amino-3- chloro-1,4-naphthoquinone (product of Wako Pure Chemical Industries, Ltd.) were employed as test substances. Through the aforementioned procedure, β-hexosaminidase release inhibition tests were performed.

In Comparative Examples 1 to 3, vitamin K1 (phylloquione, product of Wako Pure Chemical Industries, Ltd.), vitamin K2 (menaquinone, product of SIGMA), and 1,3-naphthalenediol (product of Wako Pure Chemical Industries, Ltd.) were employed as test substances. Through the aforementioned procedure, β-hexosaminidase release inhibition tests were performed.

Figure 2:
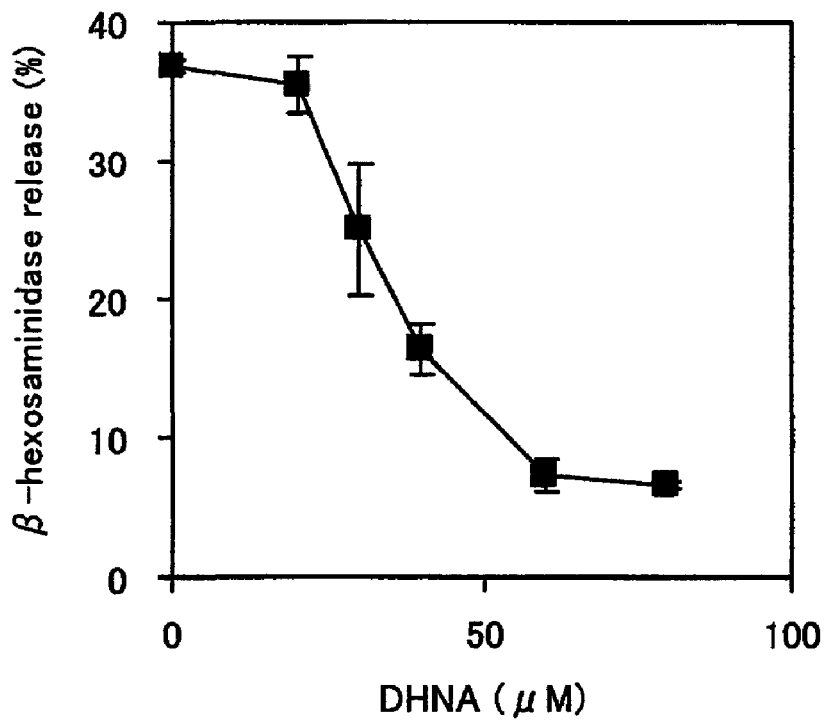
FIG. 2 Percent β-hexosaminidase release values when DHNA was administered.

As shown in FIGS. 1 and 2, each percent β-hexosaminidase release was suppressed to about 20% that of each sample containing no test substance (0 μM), when the 2-amino-3-carboxy-1,4-naphthoquinone (ACNQ) (Example 1) concentration was ≧0.4 μM, and 1,4-dihydroxy-2-naphthoic acid (DHNA) (Example 2) was ≧60 μM.

Table 1 shows 50% β-hexosaminidase release inhibitory concentrations ($IC_{50}$) of the test substances (Examples 1 to 6 and Comparative Examples 1 to 3).

Among the test substances, 2-amino-3-carboxy-1,4-naphthoquinone (ACNQ) exhibited a remarkably potent activity, with $IC_{50}$ being 0.25 μM (0.0545 μg/mL). 2-Amino-3-chloro-1,4-naphthoquinone exhibited an $IC_{50}$ of 6.8 μM (1.4 μg/mL), 4-amino-2-methyl-1-naphthol (vitamin K5) and 1,4-naphthoquinone exhibited an $IC_{50}$ of about 30 μM (6.1 and 4.7 μg/mL, respectively), and 1,4-dihydroxy-2-naphthoic acid (DHNA) and 2-methyl-1,4-naphthoquinone (vitamin K3) exhibited an $IC_{50}$ of about 50 μM (8.2 and 11.5 μg/mL, respectively).

Non-Patent Document 1 discloses that epigallocatechin gallates, some of which has an O-methyl group and some of which are components of tea, exhibits a degranulation-inhibiting effect. In the document, the degranulation-inhibiting effect is evaluated on the basis of release of histamine, and a concentration of 105.8 μM (50 μg/mL) results in about 50% percent inhibition. Non-Patent Document 2 discloses that tranilast (N-(3,4-dimethoxycinnamoyl)anthranilic acid) and ketotifen fumarate (4-(1-methyl-4-piperidylidene-4H-benzo[4,5]-cyclohepta[1,2-b]-thiophen-10(9H)-one hydrogen fumarate), which are synthetic anti-allergic agents, exhibit $IC_{50}$ to basophil-like cells (RBL-2H3) of 492 μM (161 μg/mL) and 214 μM (91 μg/mL), respectively.

Therefore, the active ingredients of the present invention exhibit a remarkably potent degranulation-inhibiting effect.

TABLE 1

$IC_{50}$ of test substances in β-hexosaminidase release inhibition test

|  | Substance | $IC_{50}$ |
| --- | --- | --- |
| Ex. 1 | ACNQ | 0.25 μM (0.0545 μg/mL) |
| Ex. 2 | DHNA | 41 μM (8.2 μg/mL) |
| Ex. 3 | Vitamin K3 | 66.8 μM (11.5 μg/mL) |
| Ex. 4 | Vitamin K5 | 29.2 μM (6.1 μg/mL) |
| Ex. 5 | 1,4-Naphthoquione | 29.8 μM (4.7 μg/mL) |
| Ex. 6 | 2-Amino-3-chloro-1,4-naphthoquinone | 6.8 μM (1.4 μg/mL) |
| Comp. Ex. 1 | Vitamin K1 | >100 μM (>45.1 μg/mL) |
| Comp. Ex. 2 | Vitamin K2 | >100 μM (>44 μg/mL) |
| Comp. Ex. 3 | 1,3-Naphthalenediol | >100 μM (>16 μg/mL) |

<PCA Reaction>

ICR mice (female, 6-week old) were preliminarily bred and grouped into the following three groups such that these groups had the same average body weight: Group 1, 0.5% carboxy-methyl-cellulose (CMC) sodium-administered group (Comparative Example 4); Group 2, ACNQ (100 μg/kg)-administered group (Example 7); and Group 3, PCA-non-induced group (Comparative Example 5). Groups 1 and 2 each included 8 mice, and Group 3 included 4 mice. Group 1 (CMC sodium-administered group) served as a control group with respect to Group 2 (ACNQ-administered group).

To each of the ICR mice of Groups 1 and 2, an anti-DNP-IgE antibody (100 ng/body) was intradermally administered through an ear auricle. Instead of the anti-DNP-IgE antibody, physiological saline was administered in a similar manner to each of the ICR mice of Group 3. Twenty-three hours after administration of the anti-DNP-IgE antibody through the ear auricle, 0.5% aqueous CMC sodium solution (test substance) was perorally administered to each of the ICR mice of Groups 1 and 3, while ACNQ (test substance) suspension in 0.5% aqueous CMC sodium solution was perorally administered to each of the ICR mice of Group 2.

Subsequently, one hour after administration of each test substance, DNP-bound BSA (0.25 mg/body) serving as an antigen and Evans Blue were intravenously administered to each of the ICR mice of Groups 1 to 3, to thereby induce PCA. Thirty minutes after induction of PCA, the ICR mice of Groups 1 to 3 were slaughtered, and the ear auricles were cut from the mice. The cut ear auricles obtained from the groups were incubated overnight at 37° C. in the presence of 1N potassium hydroxide, and Evans Blue was extracted from the incubation product with an acetone-0.5N phosphoric acid (13:5) mixture. The absorbance of each extract at 620 nm was determined, to thereby calculate the Evans Blue level leaked to the ear auricle.

Figure 3:
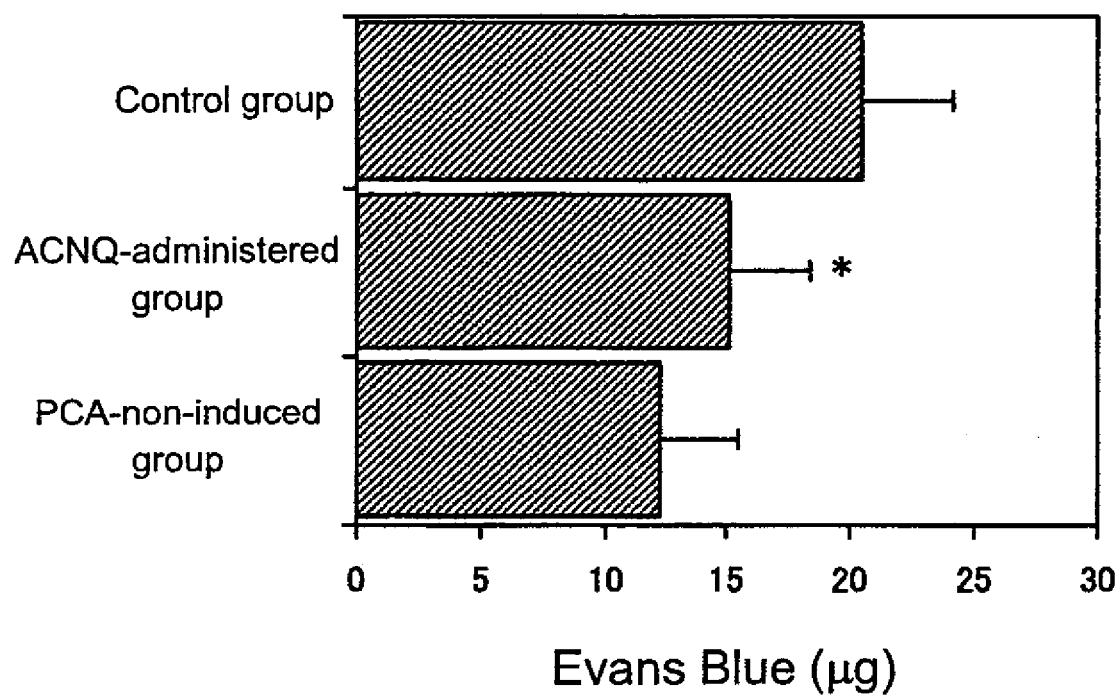
FIG. 3 Amounts of Evans blue leakage to ear auricles induced by PCA reaction among ACNQ-administered group (Example 7), CMC Na-administered group (Comparative Example 4), and PCA-non-induced group (Comparative Example 5) (*$P<0.05$, t-test, comparison with the control group (CMC Na-administered group (Comparative Example 4).

FIG. 3 shows the Evans Blue levels of the ACNQ-administered group (Example 7), the CMC sodium-administered group (control group, Comparative Example 4), and the PCA-non-induced group (Comparative Example 5).

The Evans Blue of the ACNQ-administered group (Example 7) was significantly lowered as compared with that of the CMC sodium-administered group (Comparative Example 4), indicating that ACNQ suppresses PCA reaction.

The invention claimed is:

1. A method for treating allergy, comprising administering to a subject in need thereof a therapeutically effective amount of a composition comprising one or more species selected from the group consisting of 2-amino-3-carboxy-1,4-naphthoquinone, 1,4-dihydroxy-2-naphthoic acid, and a salt thereof, wherein the allergy is allergic rhinitis or allergic dermatitis.

2. The method according to claim 1, wherein the composition comprises 2-amino-3-carboxy-1,4-naphthoquinone or a salt thereof.

3. The method according to claim 1, wherein the composition comprises 1,4-dihydroxy-2-naphthoic acid or a salt thereof.

4. The method according to claim 1, wherein the allergy is allergic rhinitis.

5. The method according to claim 1, wherein the allergy is allergic dermatitis.

* * * * *